(12) United States Patent
Song (10) Patent No.: US 10,149,688 B2
(45) Date of Patent: Dec. 11, 2018

(54) ANATOMIC ACETABULAR POSITIONING DEVICE FOR HIP ARTHROPLASTY

(71) Applicant: Benjamin Soo-il Song, Los Angeles, CA (US)

(72) Inventor: Benjamin Soo-il Song, Los Angeles, CA (US)

(73) Assignees: Benjamin S. Song, Los Angeles, CA (US); Jennifer J. Song, Los Angeles, CA (US); Angela Y. Song, Los Angeles, CA (US); Michael A. Song, Los Angeles, CA (US)

( * ) Notice: Subject to any disclaimer, the term of this patent is extended or adjusted under 35 U.S.C. 154(b) by 93 days.

(21) Appl. No.: 15/347,172

(22) Filed: Nov. 9, 2016

(65) Prior Publication Data

US 2018/0125676 A1    May 10, 2018

(51) Int. Cl.
*A61B 17/17* (2006.01)

(52) U.S. Cl.
CPC ...... *A61B 17/1742* (2013.01); *A61B 17/1739* (2013.01)

(58) Field of Classification Search
CPC . A61B 17/17; A61B 17/1703; A61B 17/1735; A61B 17/1739; A61B 17/1742; A61B 17/1746; A61B 17/175; A61B 17/1753
See application file for complete search history.

(56) References Cited

U.S. PATENT DOCUMENTS

| | | | | |
|---|---|---|---|---|
| 8,808,302 | B2 * | 8/2014 | Roose | A61B 17/1746 606/96 |
| 8,992,538 | B2 * | 3/2015 | Keefer | A61B 17/1746 606/81 |
| 9,168,048 | B2 * | 10/2015 | Roose | A61B 17/1746 |
| 9,301,858 | B2 * | 4/2016 | Barsoum | A61F 2/4657 |
| 9,439,659 | B2 * | 9/2016 | Schoenefeld | A61B 17/1757 |
| 9,492,182 | B2 * | 11/2016 | Keefer | A61B 17/1746 |
| 9,498,233 | B2 * | 11/2016 | Eash | A61B 17/1746 |
| 9,517,145 | B2 * | 12/2016 | Meridew | A61F 2/4609 |
| 9,693,785 | B2 * | 7/2017 | Theiss | A61B 17/175 |
| 9,763,682 | B2 * | 9/2017 | Bettenga | A61B 17/1746 |
| 9,820,868 | B2 * | 11/2017 | Witt | A61F 2/4609 |
| 2006/0058886 | A1 * | 3/2006 | Wozencroft | A61B 17/1746 623/22.15 |

(Continued)

*Primary Examiner* — Eric S Gibson
(74) *Attorney, Agent, or Firm* — John K. Park; Park Law Firm (57) ABSTRACT

A positioning device for acetabular procedures is provided. The positioning device for acetabular procedures includes a base plate, a central pin guide hole, a first positioning hole, and a second positioning hole. The central pin guide hole is provided through a central portion of the base plate and configured for guiding a center pin to be disposed in a specific portion of an acetabulum of a patient. The first positioning hole is provided through a first edge portion of the base plate and configured for guiding a first stabilizing pin. The second positioning hole is provided through a second edge portion of the base plate and configured for guiding a second stabilizing pin. The positioning device further includes a third positioning hole provided through a third edge portion of the base plate and configured for guiding a third stabilizing pin.

8 Claims, 11 Drawing Sheets

(56) References Cited

U.S. PATENT DOCUMENTS

| | | | | |
|---|---|---|---|---|
| 2010/0082035 | A1* | 4/2010 | Keefer | A61B 17/1746 606/91 |
| 2010/0274253 | A1* | 10/2010 | Ure | A61B 17/1746 606/91 |
| 2011/0184419 | A1* | 7/2011 | Meridew | A61B 17/151 606/80 |
| 2011/0224674 | A1* | 9/2011 | White | A61B 17/1617 606/91 |
| 2012/0041445 | A1* | 2/2012 | Roose | A61B 17/1746 606/96 |
| 2012/0226283 | A1* | 9/2012 | Meridew | A61B 17/1659 606/81 |
| 2013/0211407 | A1* | 8/2013 | Geebelen | A61B 17/1631 606/80 |
| 2013/0245631 | A1* | 9/2013 | Bettenga | A61B 17/1666 606/91 |
| 2014/0088603 | A1* | 3/2014 | Roose | A61F 2/4609 606/91 |
| 2014/0163565 | A1* | 6/2014 | Bollinger | A61B 17/1746 606/91 |
| 2014/0228854 | A1* | 8/2014 | Witt | A61B 17/1746 606/96 |
| 2014/0236160 | A1* | 8/2014 | Barsoum | A61F 2/4657 606/91 |
| 2014/0276870 | A1* | 9/2014 | Eash | A61B 17/1746 606/91 |
| 2014/0276873 | A1* | 9/2014 | Meridew | A61F 2/4609 606/91 |
| 2014/0316416 | A1* | 10/2014 | Liu | A61B 17/1746 606/87 |
| 2014/0358154 | A1* | 12/2014 | Roose | A61B 17/1746 606/96 |
| 2015/0012001 | A1* | 1/2015 | Theiss | A61B 17/175 606/87 |
| 2015/0105783 | A1* | 4/2015 | Clarke | A61B 17/1746 606/91 |
| 2015/0112348 | A1* | 4/2015 | Schoenefeld | A61B 17/1746 606/87 |
| 2015/0190151 | A1* | 7/2015 | Budhabhatti | A61B 17/1666 606/96 |
| 2015/0196307 | A1* | 7/2015 | Keefer | A61B 17/1746 606/81 |
| 2015/0297248 | A1* | 10/2015 | Gillman | A61F 2/34 606/87 |
| 2016/0287408 | A1* | 10/2016 | Witt | A61F 2/34 |
| 2017/0112510 | A1* | 4/2017 | Gillman | A61B 17/1746 |
| 2017/0112628 | A1* | 4/2017 | Dressler | A61F 2/34 |
| 2017/0258480 | A1* | 9/2017 | Liu | A61B 17/1746 |
| 2017/0281201 | A1* | 10/2017 | Theiss | A61B 17/175 |
| 2018/0078265 | A1* | 3/2018 | Eash | A61F 2/4609 |

\* cited by examiner

ANATOMIC ACETABULAR POSITIONING DEVICE FOR HIP ARTHROPLASTY

BACKGROUND OF THE INVENTION

The present invention relates to an ANATOMIC ACETABULAR POSITIONING DEVICE FOR hip arthroplasty, or a positioning device for acetabular procedures. More particularly, this invention relates to a positioning device for acetabular procedures, which helps a surgeon to perform acetabular procedures.

A need for a positioning device for acetabular procedures has been present for a long time considering the expansive demands in the everyday life. This invention is directed to solve these problems and satisfy the long-felt need.

SUMMARY OF THE INVENTION

The present invention contrives to solve the disadvantages of the prior art.

An object of the invention is to provide a positioning device for acetabular procedures.

Another object of the invention is to provide a positioning device for acetabular procedures, which helps a surgeon to position in performing acetabular procedures.

An aspect of the invention provides a positioning device for acetabular procedures.

The positioning device for acetabular procedures includes a base plate, a central pin guide hole, a first positioning hole, and a second positioning hole.

The base plate has a top surface portion, a bottom surface portion, and side edge portion connecting the top surface portion and the bottom surface portion.

The central pin guide hole is provided through a central portion of the base plate and configured for guiding a center pin to be disposed in a specific portion of an acetabulum of a patient.

The first positioning hole is provided through a first edge portion of the base plate and configured for guiding a first stabilizing pin.

The second positioning hole is provided through a second edge portion of the base plate and configured for guiding a second stabilizing pin.

The positioning device may further comprise a third positioning hole provided through a third edge portion of the base plate and configured for guiding a third stabilizing pin.

The first positioning hole may be provided approximately at 12 o'clock direction configured for being fixed at a portion of ilium and the second positioning hole is provided approximately at 6 o'clock direction configured for being fixed at a portion of ischium.

The third positioning hole may be provided approximately at 8½ o'clock direction configured for being fixed at a portion of pubic bone.

The base plate may have a substantially circular shape.

The circular shape of the base plate may have a diameter large enough to cover an opening of the acetabulum.

Each of the first, second, and third positioning holes may be provided through an edge portion of the base plate, and the edge portion protrudes from a circumferential portion of the base plate.

The central pin guide hole may be provided through a cylindrical protrusion protruding vertically from the top surface portion of the base plate.

The base plate may further comprise a side cutout portion from the central pin guide hole to the outer edge portion of the base plate.

The gap of the side cutout portion may be smaller than the diameter of the central pin guide hole.

The first positioning hole may be provided approximately at 12 o'clock direction configured for being fixed at a portion of ilium and the second positioning hole is provided approximately at 8½ o'clock direction configured for being fixed at a portion of pubic bone.

The advantages of the present invention are: the positioning device for acetabular procedures according to the invention can provide:

(1) helping the surgeon in positioning for an acetabular procedures; and (2) positioning a reamer for the acetabular procedures with a device with a simple structure.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION EMBODIMENTS OF THE INVENTION

Computer navigated patient specific custom mold is provided for anatomic acetabular preparation.

The device is prepared through MRI/CT scan and this device is patient specific accurate pin centering guide.

The device includes custom molded acetabular portion with central pin guided hole, reamer guide device, and reamer with center hole.

After surgical open of the hip joint, the acetabular portion is placed in prenavigated corresponding acetabular cavity, and stablizing pins at 12 o'clock in ilium, 6 o'clock in ischium, and 8½ o'clock in pubic bone.

(1) First Option: a guide pin is introduced to center of acetabulum in depth of acetabular wall through the center hole of the device after removed the device, reaming acetabulum with central holes, reamer along the guide pin.

(2) Second Option: after removed the first device (acetabular occupying device), the second device (reamor guide device) is placed along the corresponding stabilizing pins at ilium, ischium, and pubic bone, reaming acetabulum along the reamer guide groove.

FIGS. 1 to 6 show positioning devices 100 according to the invention.

An aspect of the invention provides a positioning device 100 for acetabular procedures.

Figure 4:
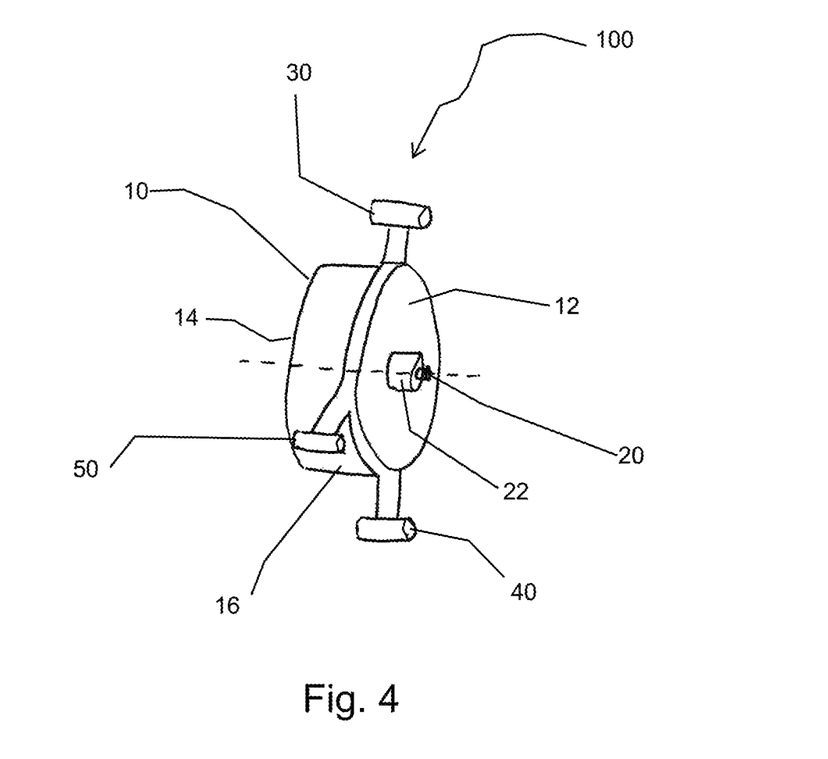
FIG. 4 is a perspective view showing a positioning device according to an embodiment of the present invention.
Figure 5:
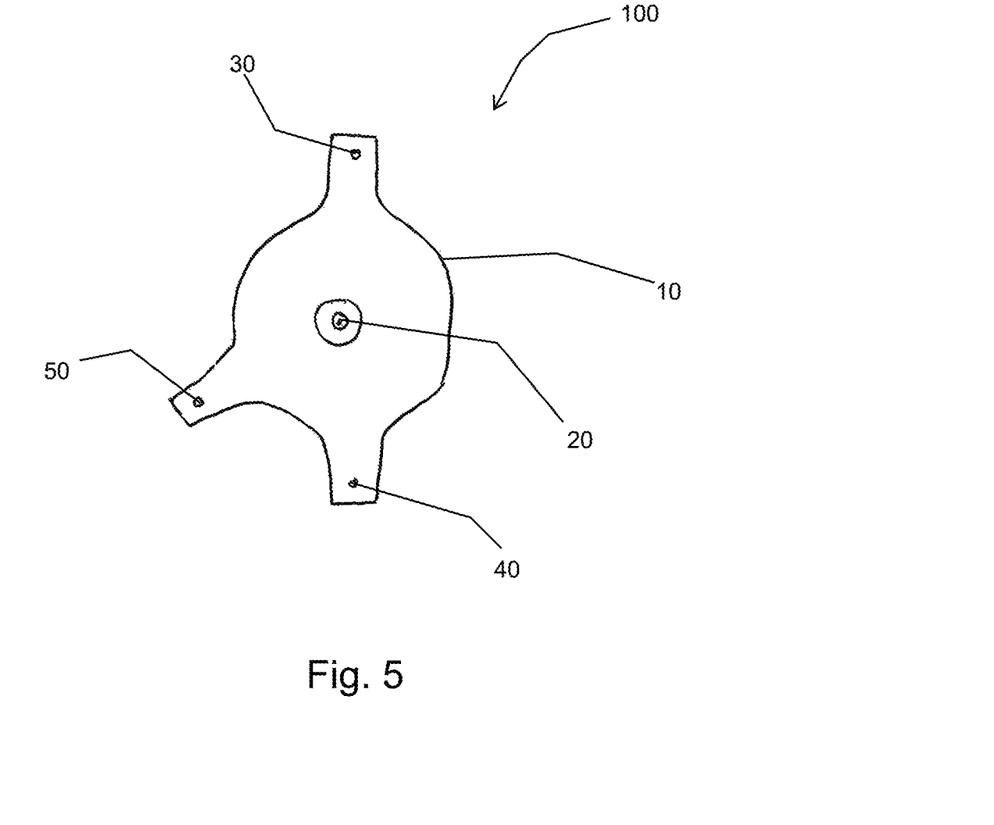
FIG. 5 is a top plan view showing the positioning device of FIG. 4.

The positioning device 100 for acetabular procedures includes a base plate 10, a central pin guide hole 20, a first positioning hole 30, and a second positioning hole 40 as shown in FIGS. 4 and 5.

The base plate 10 has a top surface portion 12, a bottom surface portion 14, and side edge portion 16 connecting the top surface portion 12 and the bottom surface portion 12 as shown in FIG. 4.

Figures 1, 2, 3:
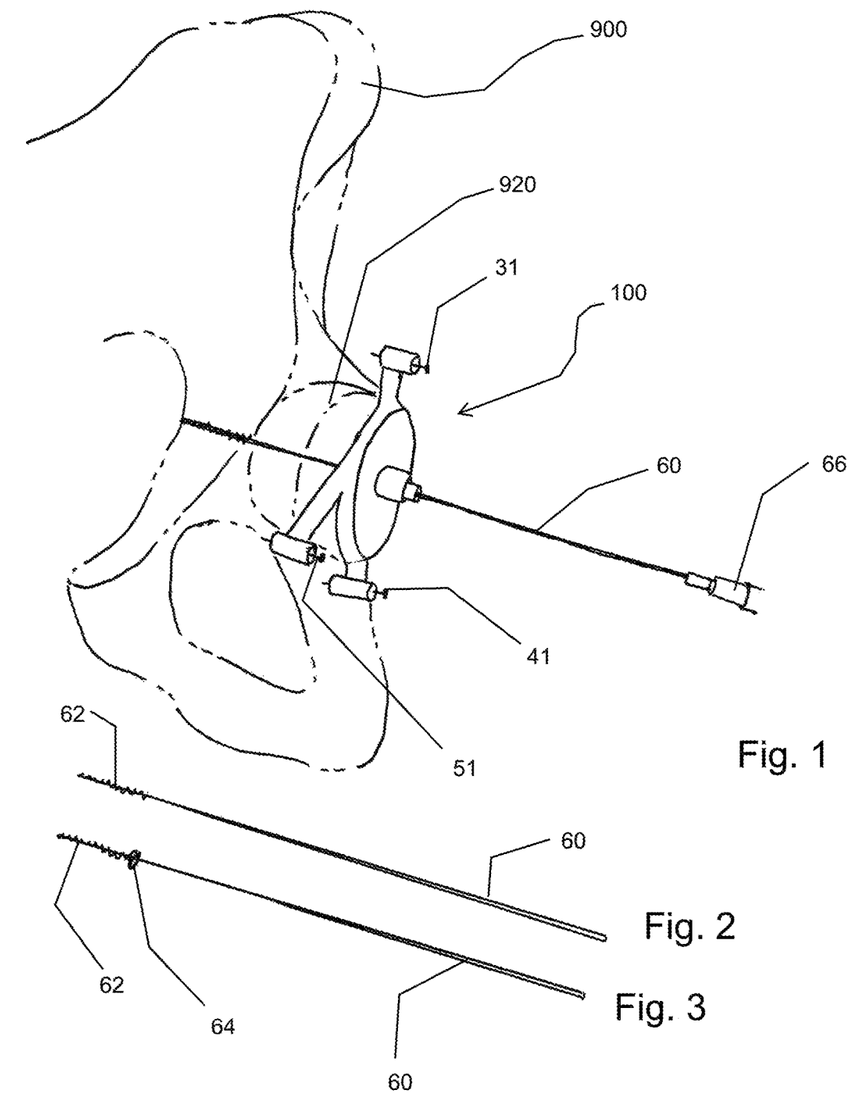
FIG. 1 is a perspective view showing a positioning device installed to the acetabulum according to an embodiment of the present invention.
FIG. 2 is a perspective view showing a type of a center pin to be positioned by the positioning device according to an embodiment of the present invention.
FIG. 3 is another perspective view showing a type of a center pin to be positioned by the positioning device according to another embodiment of the present invention.

The central pin guide hole 20 is provided through a central portion of the base plate 10 and configured for guiding a center pin 60 to be disposed in a specific portion of an acetabulum 920 of a patient as shown in FIG. 1.

The first positioning hole 30 is provided through a first edge portion of the base plate 10 and configured for guiding a first stabilizing pin 31 as shown in FIG. 1.

The second positioning hole 40 is provided through a second edge portion of the base plate 10 and configured for guiding a second stabilizing pin 41 as shown in FIG. 1.

The positioning device 100 may further comprise a third positioning hole 50 provided through a third edge portion of the base plate 10 and configured for guiding a third stabilizing pin 51 as shown in FIG. 1.

The first positioning hole 30 may be provided approximately at a superior direction configured for being fixed at a portion of ilium 930 and the second positioning hole 40 is provided approximately at an inferior direction configured for being fixed at a portion of ischium 940.

In certain embodiments of the invention, the superior direction may be a 12 o'clock direction.

In certain embodiments of the invention, the inferior direction may be a 6 o'clock direction.

The third positioning hole 50 may be provided approximately at a posterior direction configured for being fixed at a portion of pubic bone.

In certain embodiments of the invention, the posterior direction may be an 8½ o'clock direction.

The base plate 10 may have a substantially circular shape as shown in FIG. 4.

Figure 6:
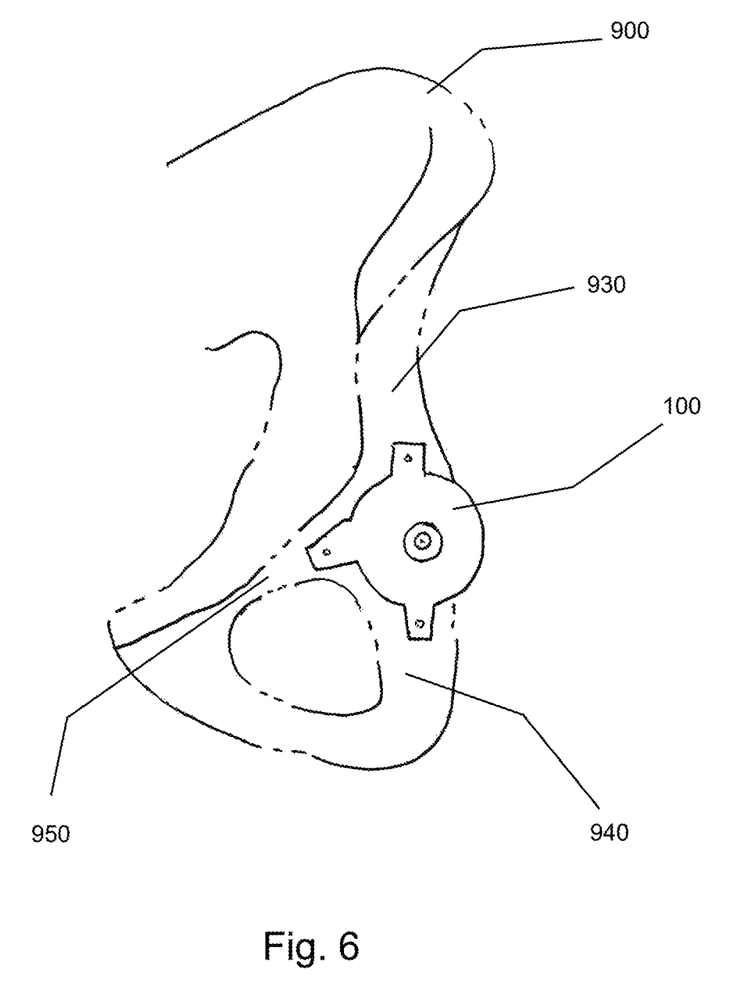
FIG. 6 is a top plan view showing a positioning device installed to the acetabulum according to an embodiment of the present invention.

The circular shape of the base plate 10 may have a diameter large enough to cover an opening of the acetabulum 920 as shown in FIG. 6.

Each of the first, second, and third positioning holes 30, 40, 50 may be provided through an edge portion of the base plate 10, and the edge portion protrudes from a circumferential portion of the base plate 10 as shown in FIG. 4.

In certain embodiments of the invention, one or two, or none of the first, second, and third positioning holes 30, 40, 50 may protrude from a circumferential portion of the base plate 10.

The central pin guide hole 20 may be provided through a cylindrical protrusion 22 protruding vertically from the top surface portion of the base plate 10 as shown in FIG. 4. Of course, in certain embodiments of the invention, the cylindrical protrusion 22 can be omitted, so that the central pin guide hole 20 is provided through the flat top surface portion 12 of the base plate 10.

Figures 7, 8:
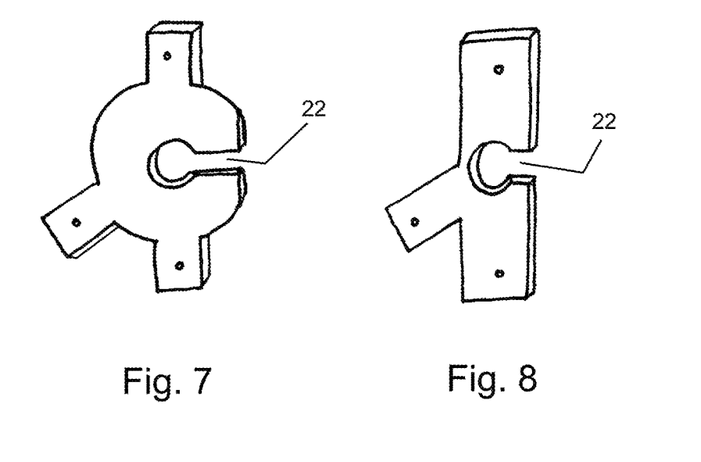
FIG. 7 is a perspective front view showing a positioning device with three positioning holes and a side cutout according to an embodiment of the present invention.
FIG. 8 is another perspective front view showing a positioning device with three positioning holes and a side cutout according to another embodiment of the present invention.

The base plate 10 may further comprise a side cutout portion 18 from the central pin guide hole 20 to the outer edge portion of the base plate 10 as shown in FIG. 7.

Figure 9:
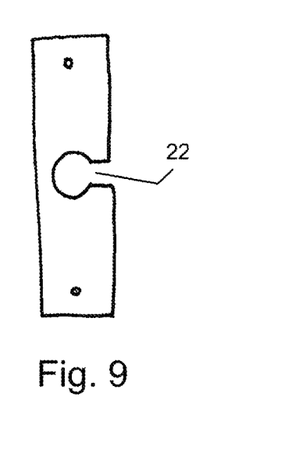
FIG. 9 is still another perspective front view showing a positioning device with two positioning holes and a side cutout according to still another embodiment of the present invention.
Figure 10:
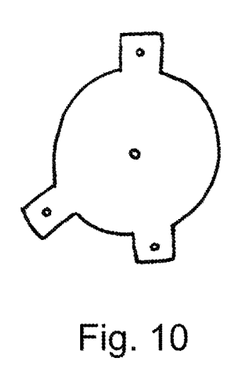
FIG. 10 is a perspective front view showing a positioning device with three positioning holes according to an embodiment of the present invention.
Figure 11:
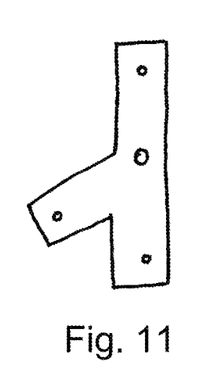
FIG. 11 is another perspective front view showing a positioning device with three positioning holes according to another embodiment of the present invention.
Figure 17:
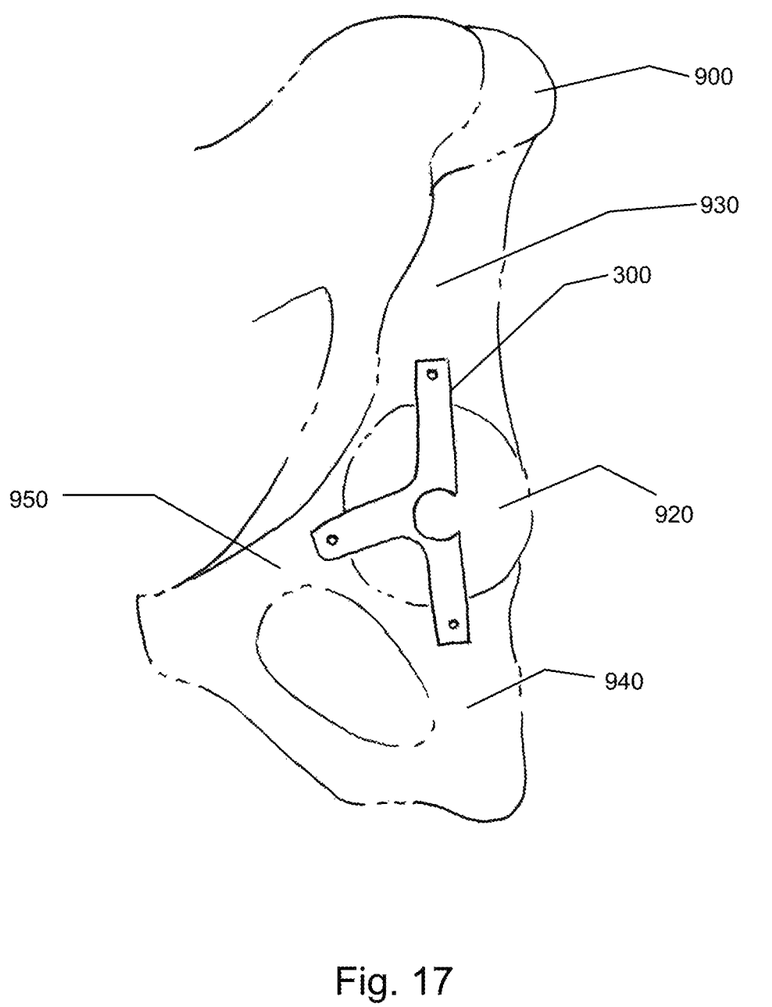
FIG. 17 is another perspective view showing the patient specific instrument for a durable resurfacing hip replacement device of FIG. 15 detached from the bones.

In certain embodiments of the invention, the base plate 10 with the side cutout portion 18, shown in FIGS. 7-9, may be adapted to the reamer guide 300 as shown in FIG. 17. These cases correspond to the Second Option described on Page 8 of this Specification.

The gap of the side cutout portion 18 may be smaller than the diameter of the central pin guide hole 20.

Figure 13:
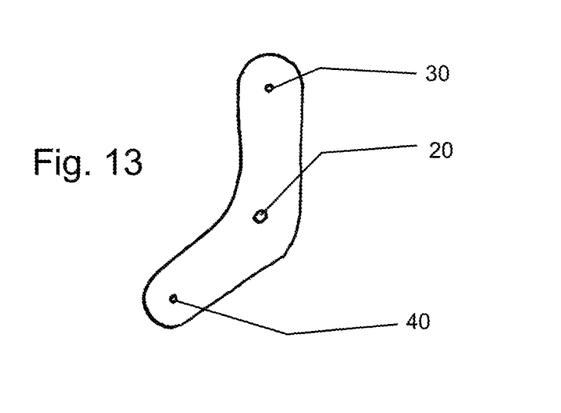
FIG. 13 is still another perspective front view showing a positioning device with two positioning holes according to still another embodiment of the present invention.

The first positioning hole 30 may be provided approximately at a superior direction configured for being fixed at a portion of ilium 930 and the second positioning hole 40 is provided approximately at a posterior direction configured for being fixed at a portion of pubic bone 950 as shown in FIG. 13.

Figure 12:
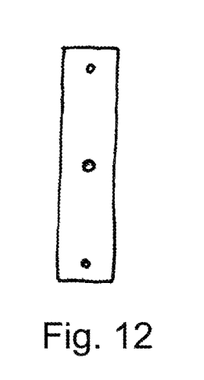
FIG. 12 is still another perspective front view showing a positioning device with two positioning holes according to still another embodiment of the present invention.

In certain embodiments of the invention as shown in FIGS. 7-13, the number of positioning holes can be changed. As shown in FIGS. 9, 12, and 13, for example, the positioning device 100 may have only two positioning holes. Compared to FIGS. 7 and 10, either one at the 6 o'clock direction or at the 8½ o'clock direction may be omitted.

As shown in FIG. 4, the base plate 10 may have a specific thickness and further a specific curved surface on the bottom surface portion 14 for accommodating to the shape of acetabulum 920. Also, the center pin 60 is queued through the central pin guide hole 20 and penetrates into fixed in the bone structure through a fastening portion 62 such as screw portion using a tool 66 as shown in FIG. 1. Also, the center pin 60 may further comprise a stopper 64 as shown in FIG. 3.

Figure 14:
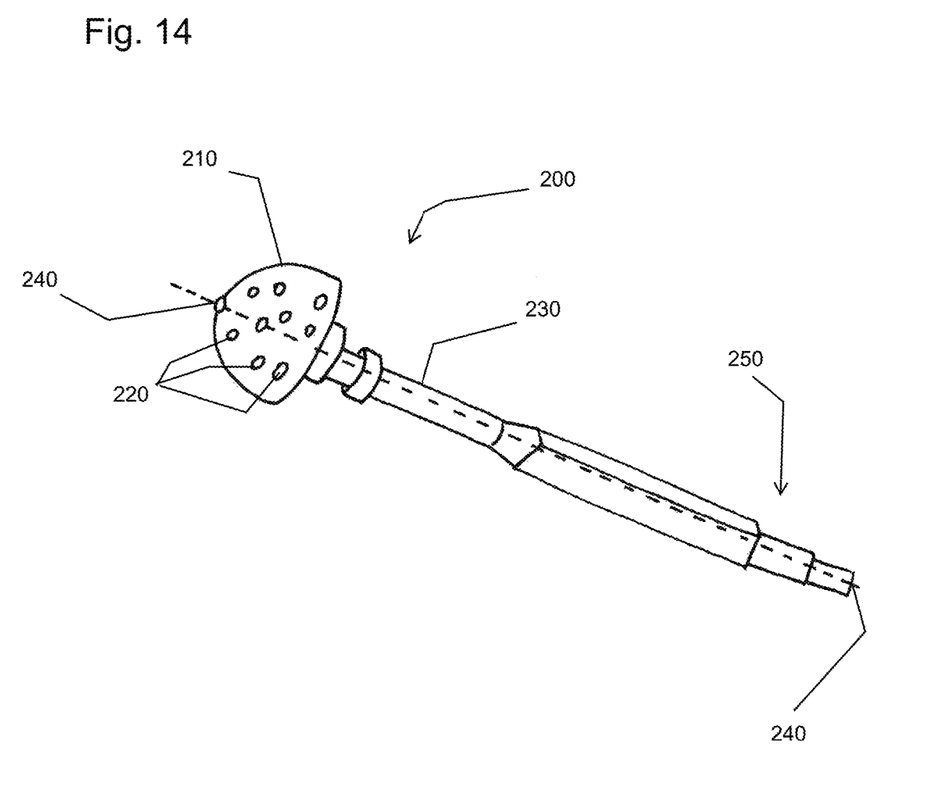
FIG. 14 is a perspective view showing directions mattered according to an embodiment of the present invention.
Figure 15:
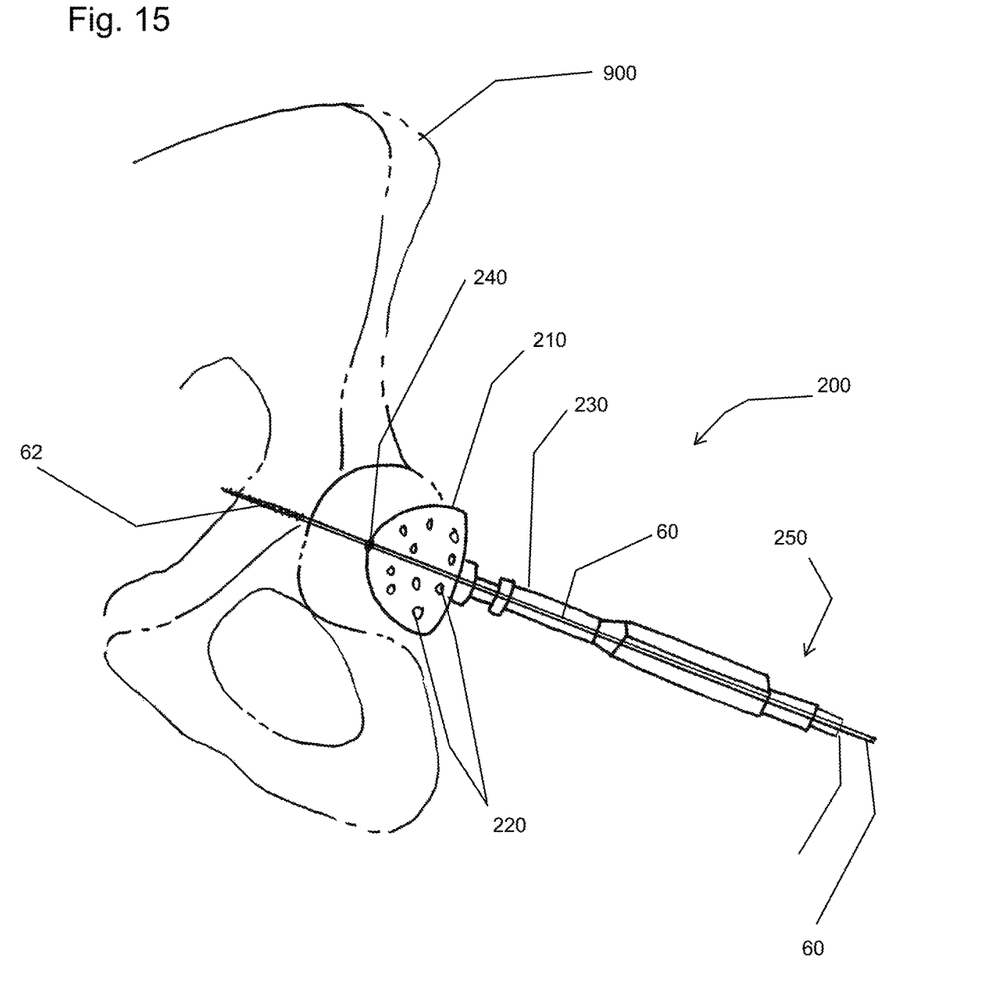
FIG. 15 is a perspective view showing a patient specific instrument for a durable resurfacing hip replacement device fitted to bones according to an embodiment of the present invention.
Figure 16:
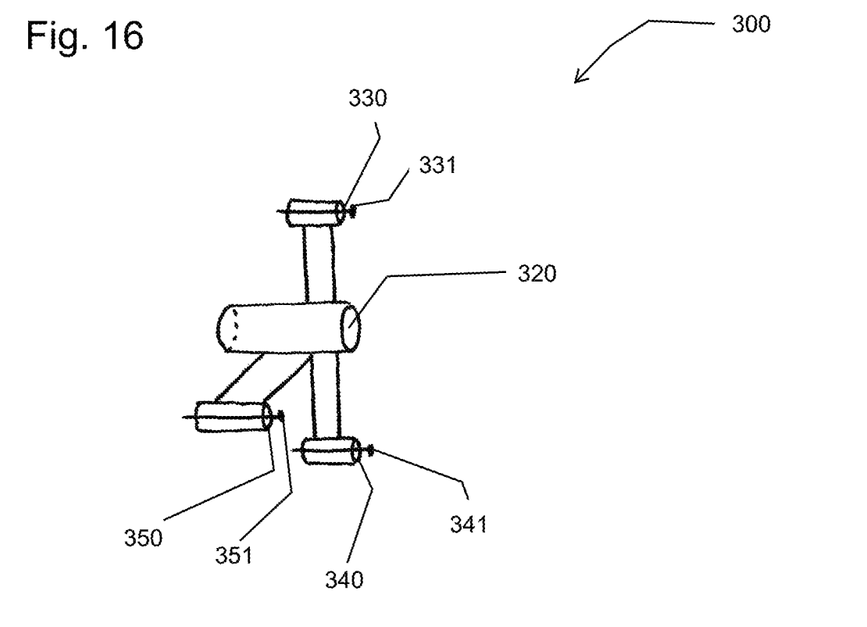
FIG. 16 is another perspective view showing a patient specific instrument for a durable resurfacing hip replacement device to be attached to the bones according to an embodiment of the present invention.
Figure 18:
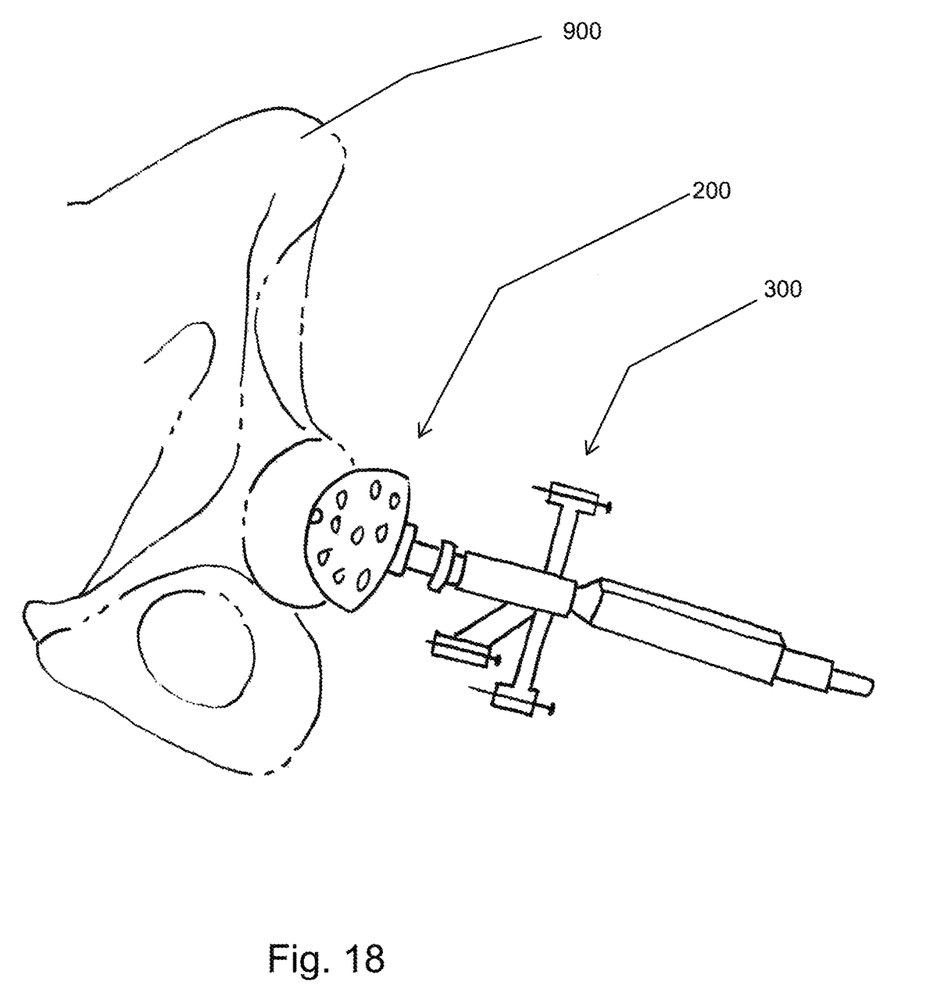
FIG. 18 is still another perspective view showing a patient specific instrument for a durable resurfacing hip replacement device fitted to the bones with directions aligned with pins in guiding drills according to an embodiment of the present invention.

FIGS. 14 and 15 show a reamer for acetabular procedures according to an embodiment of the invention, and FIGS. 16-18 show a reamer guide and a reamer for acetabular procedures according to another embodiment of the invention.

An aspect of the invention provides a reamer 200 for acetabular procedures.

A reamer 200 for acetabular procedures comprises a hemispherical head portion 210, a plurality of through-holes 220, a stem portion 230, a center hole 240, and a tool-engaging portion 250 as shown in FIGS. 14 and 15.

The plurality of through-holes 220 are bored through a shell portion of the hemispherical head portion 210.

The stem portion 230 extends from an inner peak portion of the hemispherical head portion 210 all the way down to the lower end of the reamer 200 and has a specific length.

The center hole 240 is bored through the stem portion 230 and the shell portion of the hemispherical head portion 210.

The tool-engaging portion 250 is provided at an end portion of the stem portion 230 and configured for engaging an external tool (not shown) for spinning the reamer 200.

A size of each of the plurality of through-holes 220 may be proportional to a distance from the peak portion to the position of the specific through-hole 220.

Each of the plurality of through-holes 220 may be configured for grinding a bone structure and removes the ground bone powder therethrough from an outside of the hemispherical head portion 210 to an inside of the hemispherical head portion 210.

Figure 19:
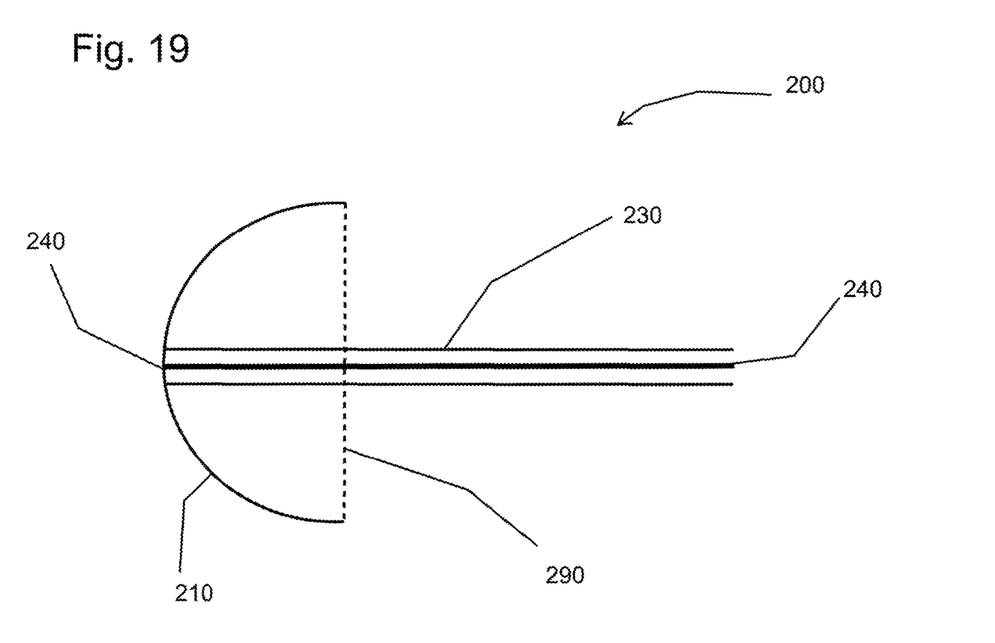
FIG. 19 is a conceptual cross-sectional view showing a reamer according to preferred embodiments of the invention.

The hemispherical head portion 210 may be hollow inside as shown in FIG. 19.

The hemispherical head portion 210 may open rearwards as shown in FIG. 19. That is, the portion 290 is a circular opening disposed around the stem portion 230.

Alternatively, the hemispherical head portion 210 may be closed rearwards by a blocking surface portion. This may be envisioned using FIG. 19. That is, the portion 290 may be the blocking surface portion having a circular plate disposed around the stem portion 230.

The stem portion 230 may have a circular cross-section.

The tool-engaging portion 250 may have a cross-section of a regular polygon.

The regular polygon may comprise a square and a hexagon.

The reamer 200 may further comprise a center pin 60 having an engaging portion 62 provided an an end portion thereof and a guiding portion extending from the engaging portion 62, and the center pin 60 is configured for being fixed to the acetabulum by the engaging portion 62 and queued through the center hole 240 by the guiding portion.

FIGS. 14 and 15 show the first option mentioned in the above. That is, the center pin 60 is installed first and then the reamer 200 is guided along the pre-installed center pin 60 and performs reaming of acetabulum as shown in FIG. 15.

The center pin 60 is to be queued through the center hole 240, which is shown by the dashed line in FIG. 14.

Another aspect of the invention provides the reamer guide 300 along with the reamer 200 as shown in FIGS. 16-18 showing the second option mentioned in the above. The reamer guide 300 in FIG. 16 is configured to be disposed around the stem portion 230 of the reamer 200 so as to position the reamer 200 more directly as shown in FIG. 18.

The reamer guide 300 can be used to position over the acetabulum 920 as shown in FIG. 17.

While the invention has been shown and described with reference to different embodiments thereof, it will be appreciated by those skilled in the art that variations in form, detail, comportions and operation may be made without departing from the spirit and scope of the invention as defined by the accompanying claims.

What is claimed is:

1. A positioning device for acetabular procedures, the positioning device comprising:
    a base plate having a top surface portion, a bottom surface portion, and a side edge portion connecting the top surface portion and the bottom surface portion;
    a central pin guide hole provided through a central portion of the base plate and configured for guiding a center pin to be disposed in a specific portion of an acetabulum of a patient;
    a first positioning hole provided through a first edge portion of the base plate and configured for guiding a first stabilizing pin;
    a second positioning hole provided through a second edge portion of the base plate and configured for guiding a second stabilizing pin; and
    a third positioning hole provided through a third edge portion of the base plate and configured for guiding a third stabilizing pin,
    wherein the first positioning hole is provided approximately at a superior direction configured for being fixed at a portion of an ilium and the second positioning hole is provided approximately at an inferior direction configured for being fixed at a portion of an ischium,
    wherein the first positioning hole is provided approximately at 12 o'clock direction configured for being fixed at a portion of ilium, the second positioning hole is provided approximately at 6 o'clock direction configured for being fixed at a portion of ischium, and the third positioning hole is provided approximately at 8½ o'clock direction configured for being fixed at a portion of pubic bone.

2. The positioning device of claim 1, wherein the third positioning hole is provided approximately at a posterior direction configured for being fixed at a portion of a pubic bone.

3. The positioning device of claim 1, wherein the base plate has a substantially circular shape.

4. The positioning device of claim 3, wherein the circular shape of the base plate has a diameter large enough to cover an opening of the acetabulum.

5. The positioning device of claim 4, wherein each of the first, second, and third positioning holes is provided through an edge portion of the base plate, and the edge portion protrudes from a circumferential portion of the base plate.

6. The positioning device of claim 3, wherein the central pin guide hole is provided through a cylindrical protrusion protruding vertically from the top surface portion of the base plate.

7. The positioning device of claim 1, wherein the base plate further comprises a side cutout portion from the central pin guide hole to an outer edge portion of the base plate.

8. The positioning device of claim 7, wherein a gap of the side cutout portion is smaller than a diameter of the central pin guide hole.

* * * * *